(12) United States Patent
Cunningham et al.

(10) Patent No.: US 11,872,301 B2
(45) Date of Patent: Jan. 16, 2024

(54) WETTING COMPOSITION INCLUDING SILICONE POLYMER SOFTENING AGENT AND WET WIPES INCLUDING THE SAME

(71) Applicant: Kimberly-Clark Worldwide, Inc., Neenah, WI (US)

(72) Inventors: Corey T. Cunningham, Larsen, WI (US); Jeffery R. Seidling, Neenah, WI (US); Stacy A. Mundschau, Weyauwega, WI (US); Paige N. Hollmaier, Neenah, WI (US); Amy L. Vanden Heuvel, Hortonville, WI (US); Anthony J. O'Lenick, Jr., Dacula, GA (US)

( * ) Notice: Subject to any disclaimer, the term of this patent is extended or adjusted under 35 U.S.C. 154(b) by 0 days.

(21) Appl. No.: 17/634,584

(22) PCT Filed: Aug. 15, 2019

(86) PCT No.: PCT/US2019/046666
§ 371 (c)(1),
(2) Date: Feb. 11, 2022

(87) PCT Pub. No.: WO2021/029893
PCT Pub. Date: Feb. 18, 2021

(65) Prior Publication Data
US 2022/0280413 A1    Sep. 8, 2022

(51) Int. Cl.
| C11D 9/36 | (2006.01) |
| A61K 8/892 | (2006.01) |
| A61Q 1/14 | (2006.01) |
| A61K 8/898 | (2006.01) |
| A61K 8/02 | (2006.01) |

(52) U.S. Cl.
CPC ............ *A61K 8/892* (2013.01); *A61K 8/0208* (2013.01); *A61K 8/898* (2013.01); *A61Q 1/14* (2013.01)

(58) Field of Classification Search
CPC .. C11D 1/82; C11D 3/162; C11D 9/36; C11D 17/041
See application file for complete search history.

(56) References Cited

U.S. PATENT DOCUMENTS

| 5,164,046 | A | 11/1992 | Ampulski et al. |
| 5,591,306 | A | 1/1997 | Kaun |
| 5,807,956 | A | 9/1998 | Czech |
| 6,054,020 | A | 4/2000 | Goulet et al. |
| 6,515,095 | B1 | 2/2003 | Omura et al. |
| 6,582,558 | B1 | 6/2003 | Liu |
| 6,599,393 | B1 | 7/2003 | Liu |
| 6,951,598 | B2 | 10/2005 | Flugge et al. |
| 7,186,318 | B2 | 3/2007 | Liu et al. |
| 8,030,226 | B2 * | 10/2011 | Bradley ................. B32B 5/26 442/99 |
| 8,367,568 | B2 | 2/2013 | Bradley et al. |
| 8,987,180 | B2 | 3/2015 | Wenzel et al. |
| 2002/0112835 | A1 | 8/2002 | Liu et al. |
| 2012/0308494 | A1 * | 12/2012 | Schubert ................. A61Q 19/00 8/405 |
| 2014/0171351 | A1 * | 6/2014 | Wenzel ................. A61Q 19/10 510/157 |
| 2017/0208798 | A1 | 7/2017 | Chaudhary et al. |

FOREIGN PATENT DOCUMENTS

| CN | 1312307 | A | 9/2001 |
| CN | 102675652 | A | 9/2012 |
| CN | 102643435 | B | 6/2014 |
| CN | 106589386 | A | 4/2017 |
| RU | 2505281 | C2 | 1/2014 |

OTHER PUBLICATIONS

Edgepark Medical Supplies, "Brava Skin Barrier Wipe, Sting-Free, Alcohol-Free, Silicone-Based", Coloplast Inc., https://www.edgepark.com/ostomy/skin-prep-and-adhesive-removers/skin-prep-wipes/brava-skin-barrier-wipe-sting-free-alcohol-free-silicone-based/p/62120215.

Wei, Yuan et al., "Synthesis of multiblock linear polyether functional amino silicone softener and its modification of surface properties on cotton fabrics", Polymer Bulletin, https://link.springer.com/article/10.1007/s00289-018-2375-1.

Fischer, Sarah C.L. et al., "Bioinspired polydimethylsiloxane-based composites with high shear resistance against wet tissue", Journal of the Mechanical Behavior of Biomedical Materials, https://www.sciencedirect.com/science/article/pii/S1751616116000175.

Sutyagin V.M. et al, "Chemistry and Physics of Polymers", 2003. (p. 142, paragraphs 1-2, p. 132, paragraphs 4-5, p. 140, paragraph 2, p. 151, paragraph 1, p. 173, paragraph 2).

\* cited by examiner

*Primary Examiner* — Charles I Boyer
(74) *Attorney, Agent, or Firm* — Kimberly-Clark Worldwide, Inc.

(57) ABSTRACT

Wetting compositions can include water and a silicone-based softening agent. The softening agent can include a structure of: $G_1$ can be —$CH_2CH_2CH_2$—($C_aH_{2a}O$)$_b$—H. $G_2$ can be —$CH_2CH_2CH_2$—$OCH_2$—$CH(OH)$—$CH_2$—$R_1$. $R_1$ can be selected from the group consisting of: —NH—($CH_2$)$_n$ —$NH_2$, —NH—($CH_2$)$_n$—NH—($CH_2$)$_m$—$NH_2$, N-piperidine, and N-3,3,5,5-tetramethyl-piperidine.

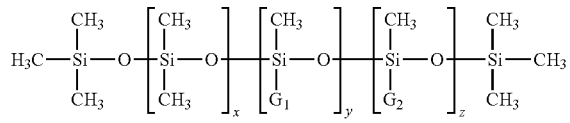

20 Claims, No Drawings

WETTING COMPOSITION INCLUDING SILICONE POLYMER SOFTENING AGENT AND WET WIPES INCLUDING THE SAME

TECHNICAL FIELD

Disclosed are wetting compositions that include a silicone polymer softening agent and wet wipes that include the same. More specifically, disclosed is wetting composition that include a silicone polymer softening agent that is water soluble or dispersible and reduces the potential for production of unwanted by-products.

BACKGROUND OF THE DISCLOSURE

Wipes including a wetting composition, commonly referred to as wet wipes, have been used in the personal care industry for numerous years. Such wipes include a basesheet, or substrate, to which the wetting composition is applied. The wetting compositions typically include a surfactant and a water base. Sample product applications for wet wipes are for skin care for cleaning the skin of a wearer of an absorbent article during the change of an absorbent article to clean the skin from body exudates, such as urine, bowel movement (BM), menses, etc. Such wipes can be configured to be flushable or non-flushable. Wet wipes can also be utilized for other general skin cleaning, such as hands and face, make-up removal, and surface cleaning, among other uses.

Wetting compositions can include various components depending on the intended end use. In end uses targeted at being used against skin, such wetting compositions may include a silicone polymer to provide a softening effect to the basesheet that can enhance the wipe experience. To be ideal for a wet wipe delivery system, a silicone polymer needs to be water soluble or highly dispersible, provide a softening effect to the basesheet, and not contain any objectionable by-products. There are many silicone polymers available for cosmetic use, but very few meet all three of these design criteria.

Thus, there remains a need for wetting compositions including a silicone agent that is water soluble or dispersible, provides a softening effect to the basesheet, and reduces the potential for production of unwanted by-products.

SUMMARY OF THE DISCLOSURE

In one aspect of the disclosure, a wetting composition is provided. The wetting composition can include water in an amount of at least 75% of the wetting composition. The wetting composition can further include a softening agent having the following structure:

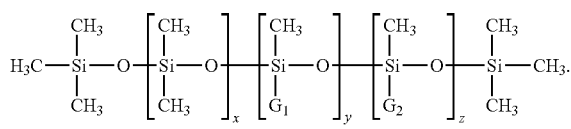

$G_1$ can be —$CH_2CH_2CH_2$—$(CaH_{2a}O)_b$—H. $G_2$ can be —$CH_2CH_2CH_2$—$OCH_2$—$CH(OH)$—$CH_2$—$R_1$. $R_1$ can be selected from the group consisting of: —NH—$(CH_2)_n$—$NH_2$, —NH—$(CH_2)_n$—NH—$(CH_2)_m$—$NH_2$, N-piperidine, and N-3,3,5,5-tetramethyl-piperidine.

In another aspect of the disclosure, a wetting composition can include water in an amount of at least 75% of the wetting composition. The wetting composition can further include a softening agent having the following structure:

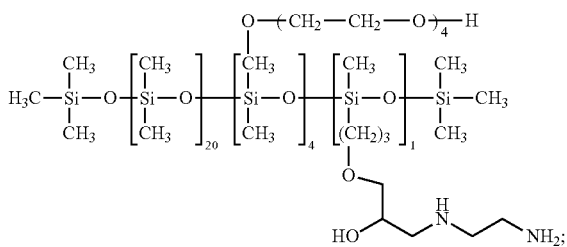

wherein x is at least 2 and is less than or equal to 50; wherein y is at least 1 and is less than 7; and wherein z is at least 1 and is less than 5.

In yet another aspect of the disclosure, a wet wipe is provided. The wet wipe can include a substrate and a wetting composition. The wetting composition can further include a softening agent having the following structure:

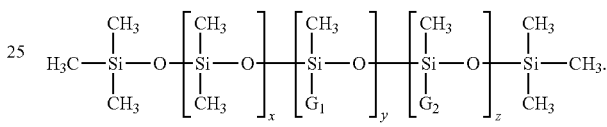

$G_1$ can be —$CH_2CH_2CH_2$—$(CaH_{2a}O)_b$—H. $G_2$ can be —$CH_2CH_2CH_2$—$OCH_2$—$CH(OH)$—$CH_2$—$R_1$. $R_1$ can be selected from the group consisting of: —NH—$(CH_2)_n$—$NH_2$, —NH—$(CH_2)_n$—NH—$(CH_2)_m$—$NH_2$, N-piperidine, and N-3,3,5,5-tetramethyl-piperidine.

DETAILED DESCRIPTION OF THE DISCLOSURE

The present disclosure is directed to wetting compositions that have been developed to address the above-described problems to be compatible for use with wet wipes. Suitable ingredients for such wetting compositions can include a carrier, such as water, and a silicone softening agent. In some embodiments, wetting compositions can include additional ingredients, some of which will be described in further detail herein, which may come from a broad category range including, but not limited to aqueous solvents, non-aqueous solvents, humectants, emollients, surfactants, emulsifiers, sequestrants, chelators, preservatives, pH modifiers (or pH adjusting ingredient), combinatorial preservatives/antimicrobial agents, disinfectants, colorants, rheology modifiers, antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, deodorants, antiperspirants, fragrance, and various other optional ingredients as are known by one skilled in the art.

Softening Agent

Softening agents of the present disclosure can include a silicone polymer of the following structure:

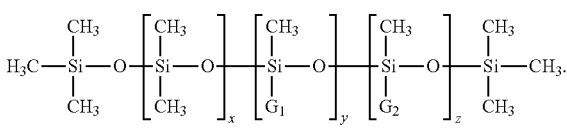

The silicone polymer can be a non-reactive polymer, which means it does not include methoxy or hydroxyl groups bonded directly to the Silicone pendant chain functionality. By creating the softening agent structure to include methyl groups that are non-reactive, compared to a functional group that is reactive (such as a methoxy or hydroxyl groups), the silicone polymer of the present disclosure can avoid unwanted by products, such as methanol. The silicone polymer can also be configured such that it is neutral, or uncharged.

Referring to the sample structure shown above from left to right, the first functional unit can have x units in the polymer chain. Preferably, the silicone polymer can be configured such that x is at least 2 and is less than or equal to 50, and more preferably, x is at least 15 and is less than or equal to 30. In some embodiments, x is at least 18 and is less than or equal to 25. The x variable can contribute to the ultimate length of the silicone polymer chain, which can impact solubility, viscosity, and the lubricity of the polymer, which can modify the feel of the polymer on a user's skin.

The second functional unit in the silicone polymer can include a $G_1$ unit and can have y units in the polymer chain. The overall polymer units in the chain for the second functional unit (y) can preferably range from at least 1 and be less than 7, and more preferably, y is at least 3 and is less than or equal to 5. $G_1$ can be $—CH_2CH_2CH_2—(C_aH_{2a}O)_b—H$. $G_1$ can be described as including a first linking group of $—CH_2CH_2CH_2—$ and can further include a first structure of $(C_aH_{2a}O)_b—H$. In some embodiments, a can be 2 such that the first structure in the second functional unit can be ethylene oxide (or polyethylene glycol, "PEG"). In other embodiments, a can be equal to 3 such that the first structure in the second functional unit can be propylene oxide (or polypropylene glycol, "PPG"). Therefore, in describing the silicone polymer of the present disclosure it is possible that a can be an average, and thus, a non-integer value. In preferred embodiments, b can range from 1 to less than 25, and is preferably at least 3 and is less than or equal to 6. It is to be noted that in cases where there are more than one second functional units (i.e., when y is greater than 1), various second functional units can be configured differently. For example, one second functional unit can be configured such that a is equal to 2 to provide ethylene oxide in that functional unit, and another second functional unit can be configured such that a is equal to 3 to provide propylene oxide. In addition, the value for b in various second functional units can vary as well.

The second functional unit can be modified to control the water solubility of the silicone polymer softening agent. For example, configuring the silicone polymer where b is a lower number can impart water dispersibility to the silicone polymer whereas configuring the silicone polymer is a higher number can impart water solubility. Additionally, PEG unit(s) can be more compatible with water than PPG units. If y is greater than one and there is at least one PEG unit and at least one PPG unit, the ratio between PEG unit(s) to PPG unit(s) can be modified as necessary to generate the desired water solubility of the polymer.

The third functional unit in the silicone polymer can include a $G_2$ unit and can have z units in the polymer chain. The overall polymer units in the chain for the third functional unit (z) can preferably range from at least 1 to be less than 5, and more preferably be at least 1 and less than or equal to 3. $G_2$ can be any suitable diamine or triamine. $G_2$ can be $—CH_2CH_2CH_2—OCH_2—CH(OH)—CH_2—R_1$. $G_2$ can be described as including a second linking group of $—CH_2CH_2CH_2—OCH_2—CH(OH)—CH_2$ and can further include a second structure, $R_1$, selected from the group consisting of: $—NH—(CH_2)_n—NH_2$, $—NH—(CH_2)_n—NH—(CH_2)_m—NH_2$, N-piperidine, and N-3,3,5,5-tetramethyl-piperidine. N-piperidine can have the following structure:

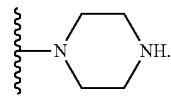

N-3,3,5,5-tetramethyl-piperidine can have the following structure:

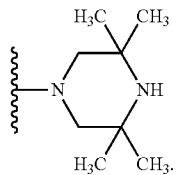

In other words, the second linking group and the second structure ($R_1$) forming $G_2$ of the third functional unit can include: '$—(CH_2)_3—OCH_2—CH(OH)—CH_2—NH(CH_2)_n—NH_2$, $—(CH_2)_3—OCH_2—CH(OH)—CH_2—NH—(CH_2)_n—NH—(CH_2)_n—NH_2$, $—(CH_2)_3—OCH_2—CH(OH)—CH_2—(N-piperidine)$, or $—(CH_2)_3—OCH_2—CH(OH)—CH_2—(N-3,3,5,5-tetramethyl-piperidine)$.

Sterically encumbered amines, such as N-piperidine and N-3,3,5,5-tetramethyl-piperidine, used as the second structure ($R_1$) as part of $G_2$ can help to prevent yellowing, but can reduce the compatibility with water so if one or more of those amines are included in the silicone polymer, the silicone polymer can be adjusted to include a greater amount of y monomers in the second functional unit and/or larger values of b in the first structure in the second functional unit. In some embodiments, a $G_2$ unit can be configured such that n in $R_1$ is at least 2 and is less than 7. In some embodiments, a $G_2$ unit can configured such that m in $R_1$ is at least 2 and is less than 7. In one preferred embodiment, at least one $G_2$ unit can be configured to be $—NH—(CH_2)_2—NH_2$ (ethylene diamine). Similar to the discussion above with respect to the second functional unit, if there is more than one third functional unit in the polymer chain (i.e., when z is greater than 1), the third functional units can be configured differently from one another. The third functional unit in the silicone polymer chain can influence the deposition performance of the silicone polymer to the base substrate, and thus, can affect the feel of softness of a wipe against a user's skin.

The silicone polymer softening agent can also be configured with a particular ratio of x to (y+z). For example, in some embodiments, the ratio of x to (y+z) can be at least 2:1 and can be less than 9:1. More preferably, the ratio of x to (y+z) can be at least 2:1 and less than 6:1.

A benefit to the silicone polymer softening agent of the present disclosure is that it provides two different mechanisms to manipulate the softness and solubility of the silicone polymer. As described above, the second functional unit can be manipulated to control water solubility, whereas the third functional unit can be manipulated to control the deposition of the polymer on a substrate, and thus, the overall softness of a wipe including the wetting composition as felt by a user's skin. Another additional benefit to the silicone polymer structure of the present disclosure is that the methyl groups bonded to the terminal silicone groups, as well as in the first, second, and third functional units, are non-reactive and therefore reduce the potential for unwanted by-products, such as methanol.

The silicone polymers of the present disclosure can be synthesized in utilizing an exemplary procedure as disclosed in U.S. Pat. No. 5,807,956, issued to Czech, the disclosure of which is incorporated herein to the extent it is consistent herewith. In particular, the silicone polymers can be synthesized in a first step that adds the different functional units to the polymer backbone by reacting silane moieties with different allyl ethers.

As an example, this discussion will focus on the synthesis of the particular silicone polymer described as Code No. 5 in Table 2 (described in the Examples section). In a 1 L 4-neck flask equipped with a stirrer, addition funnel and reflux condenser, silane polymer Silmer H-E4 of the general formula $(CH_3)_3Si(OSi(CH_3)_2)_{20}(OSiH(CH_3))_5OSi(CH_3)_3$ can be heated to 80° C. A slow addition of a mixture of allyl glycidyl ether and allyl PEG-4 ether (1:4.4 ratio) can be started at 80° C. after chloroplatinic acid (5 to 10 ppm as Pt) was added to the flask. The temperature can be maintained at 80 to 90° C. until no SiH can be detected. The resulting fluid, Intermediate 1, has the following general structure:

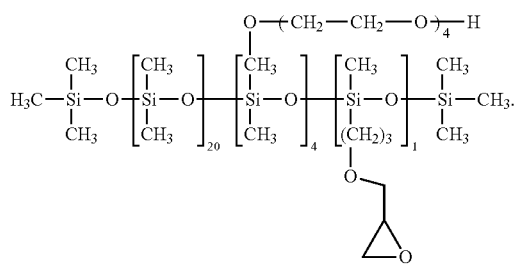

In a second step, the desired amino functional group providing the second structure for the third functional unit can be added to the polymer. This can be done by adding a solution of 50% isopropanol and ethylene diamine (1.2 mole equivalents relative to allyl glycidyl ether) to the flask, still maintaining the temperature at 80° C. The mixture can be allowed to react until no epoxy functionality can be determined by titration. All reaction solvent and any excess allyl ether and amine can be removed by vacuum strip at 50 mm Hg and 120° C. In the context of the particular silicone polymer described as Code No. 5 in Table 2 (described in the Examples section), the final silicone polymer (for Code No. 5) has the structure:

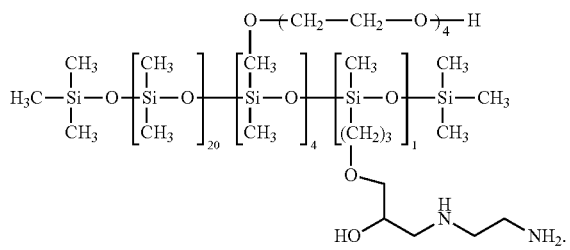

Of course, it is to be appreciated that a similar synthesis procedure can be carried out by one of skill in the art to produce silicone polymers different than Code 5 from Table 2, but encompassed by the present disclosure.

Carriers

As mentioned above, the wetting compositions of the present disclosure that can include a silicone polymer as a softening agent may be formulated with one or more conventional and compatible carrier materials. The wetting composition may take a variety of forms including, without limitation, aqueous solutions, gels, balms, lotions, suspensions, creams, milks, salves, ointments, sprays, emulsions, oils, resins, foams, solid sticks, aerosols, and the like. Liquid carrier materials suitable for use in the instant disclosure include those well-known for use in the cosmetic, pharmaceutical, and medical arts as a basis for ointments, lotions, creams, salves, aerosols, gels, suspensions, sprays, foams, washes, and the like, and may be used in their established levels. The carrier can comprise from about 0.01% to about 99.98% (by total weight of the composition), depending on the carrier used.

Preferable carrier materials include polar solvent materials, such as water. For instance, where the wetting composition is a wetting composition, such as described below for use with a wet wipe, the composition will typically include water. The wetting compositions can suitably comprise water in an amount of from about 0.01% (by total weight of the composition) to about 99.98% (by total weight of the composition), or from about 1.00% (by total weight of the composition) to about 99.98% (by total weight of the composition), or from about 50.00% (by total weight of the composition) to about 99.98% (by total weight of the composition), or from about 75.00% (by total weight of the composition) to about 99.98% (by total weight of the composition). In some embodiments, water can comprise an amount from about 50.00% (by total weight of the composition) to about 70.00% (by total weight of the composition). In some embodiments, water can comprise an amount greater than 90.00% (by total weight of the composition). In some embodiments, water can comprise at least about 91%, or at least about 92%, or at least about 93%, or at least about 94%, or at least about 95%, or at least about 96%, or at least about 97%, or at least about 98%, or at least about 99% (by total weight of the composition).

Other potential carriers include emollients, humectants, polyols, surfactants, esters, perfluorocarbons, silicones, and other pharmaceutically acceptable carrier materials.

In one embodiment, the wetting compositions can optionally include one or more emollients, which typically act to soften, soothe, and otherwise lubricate and/or moisturize the skin. Suitable emollients that can be incorporated into the compositions include oils such as alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, fatty acids, glycerol esters and derivatives, propylene glycol esters and derivatives, alkoxylated carboxylic acids, alkoxylated alcohols, fatty alcohols, and combinations thereof.

Some embodiments of the wetting compositions may include one or more emollients in an amount of from about 0.01% (by total weight of the composition) to about 20% (by total weight of the composition), or from about 0.05% (by total weight of the composition) to about 10% (by total weight of the composition), or from about 0.10% (by total weight of the composition) to about 5% (by total weight of the composition).

In some embodiments, the wetting compositions include one or more esters. The esters may be selected from cetyl palmitate, stearyl palmitate, cetyl stearate, isopropyl laurate, isopropyl myristate, isopropyl palmitate, and combinations thereof. The fatty alcohols include octyldodecanol, lauryl, myristyl, cetyl, stearyl, behenyl alcohol, and combinations thereof. The fatty acids can include, but are not limited to, capric acid, undecylenic acid, lauric acid, myristic acid, palmitic acid, stearic acid, oleic acid, linoleic acid, arachidic acid, and behenic acid. Ethers such as eucalyptol, ceteraryl glucoside, dimethyl isosorbide polyglyceryl-3 cetyl ether, polyglyceryl-3 decyltetradecanol, propylene glycol myristyl ether, and combinations thereof can also suitably be used as emollients. Other suitable ester compounds for use in the wetting compositions or the present disclosure are listed in the *International Cosmetic Ingredient Dictionary and Handbook*, 16th Edition (2016), ISBN 1-882621-55-7, and in the 2007 *Cosmetic Bench Reference*, Allured Pub. Corporation (Jul. 15, 2007) ISBN-10: 1932633278, ISBN-13: 978-1932633276, both of which are incorporated by reference herein to the extent they are consistent herewith.

Humectants that are suitable as carriers in the wetting compositions of the present disclosure include, for example, glycerin, glycerin derivatives, hyaluronic acid, hyaluronic acid derivatives, betaine, betaine derivatives, amino acids, amino acid derivatives, glycosaminoglycans, glycols, polyols, sugars, sugar alcohols, hydrogenated starch hydrolysates, hydroxy acids, hydroxy acid derivatives, salts of PCA and the like, and combinations thereof. Specific examples of suitable humectants include glycerin, honey, sorbitol, hyaluronic acid, sodium hyaluronate, betaine, lactic acid, citric acid, sodium citrate, glycolic acid, sodium glycolate, sodium lactate, urea, propylene glycol, butylene glycol, pentylene glycol, ethoxydiglycol, methyl gluceth-10, methyl gluceth-20, polyethylene glycols (as listed in the *International Cosmetic Ingredient Dictionary and Handbook* such as PEG-2 through PEG 10), propanediol, xylitol, maltitol, or combinations thereof.

The wetting compositions of the disclosure may include one or more humectants in an amount of about 0.01% (by total weight of the composition) to about 20% (by total weight of the composition), or about 0.05% (by total weight of the composition) to about 10% by total weight of the composition, or about 0.1% (by total weight of the composition) to about 5.0% (by total weight of the composition).

In an embodiment where the wetting composition serves as a wash (e.g. shampoo; surface cleaner; or hand, face, or body wash), the wetting composition will likely include one or more surfactants. In an embodiment where the wetting composition is included in a wipe, the wetting composition may also likely include one or more surfactants. These may be selected from anionic, cationic, nonionic, zwitterionic, and amphoteric surfactants. Amounts of surfactants may range from 0.01 to 30%, or from 0.05 to 20%, or from 0.10 to 15% by total weight of the composition. In some embodiments, the surfactant can comprise less than 1% by total weight of the composition.

Suitable anionic surfactants include, but are not limited to, $C_8$ to $C_{22}$ alkane sulfates, ether sulfates and sulfonates. Among the suitable sulfonates are primary $C_8$ to $C_{22}$ alkane sulfonate, primary $C_8$ to $C_{22}$ alkane disulfonate, $C_8$ to $C_{22}$ alkene sulfonate, $C_8$ to $C_{22}$ hydroxyalkane sulfonate or alkyl glyceryl ether sulfonate. Specific examples of anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate and mixtures thereof. Other anionic surfactants include the $C_8$ to $C_{22}$ acyl glycinate salts. Suitable glycinate salts include sodium cocoylglycinate, potassium cocoylglycinate, sodium lauroylglycinate, potassium lauroylglycinate, sodium myristoylglycinate, potassium myristoylglycinate, sodium palmitoylglycinate, potassium palmitoylglycinate, sodium stearoylglycinate, potassium stearoylglycinate, ammonium cocoylglycinate and mixtures thereof. Cationic counter-ions to form the salt of the glycinate may be selected from sodium, potassium, ammonium, alkanolammonium and mixtures of these cations.

Suitable cationic surfactants include, but are not limited to alkyl dimethylamines, alkyl amidopropylamines, alkyl imidazoline derivatives, quaternised amine ethoxylates, and quaternary ammonium compounds.

Suitable nonionic surfactants include, but are not limited to, alcohols, acids, amides or alkyl phenols reacted with alkylene oxides, especially ethylene oxide either alone or with propylene oxide. Specific nonionics are $C_6$ to $C_{22}$ alkyl phenols-ethylene oxide condensates, the condensation products of $C_8$ to $C_{13}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides, alkyl polysaccharides, amine oxides, block copolymers, castor oil ethoxylates, ceto-oleyl alcohol ethoxylates, ceto-stearyl alcohol ethoxylates, decyl alcohol ethoxylates, dinonyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, monobranched alcohol ethoxylates, natural alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, synthetic alcohol ethoxylates, tall oil fatty acid ethoxylates, tallow amine ethoxylates and tridecanol ethoxylates.

Suitable zwitterionic surfactants include, for example, alkyl amine oxides, alkyl hydroxysultaines, silicone amine oxides, and combinations thereof. Specific examples of suitable zwitterionic surfactants include, for example, 4-[N,N-di(2-hydroxyethyl)-N-octadecylammonio]-butane-1-carboxylate, S-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, lauryl hydroxysultaine and combinations thereof.

Suitable amphoteric surfactants include, but are not limited to, derivatives of aliphatic quaternary ammonium, phosphonium, and sulfonium compounds, in which the aliphatic radicals can be straight or branched chain, and wherein one of the aliphatic substituents contains from about 8 to about 24 carbon atoms and one substituent contains an anionic group, e.g., carboxy, sulfonate, sulfate, phosphate, or phosphonate. Illustrative amphoterics are coco dimethyl carboxymethyl betaine, cocamidopropyl betaine, coco-betaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)-alpha-carboxyethyl betaine, cocoamphoacetates, and combinations thereof. The sulfobetaines may include stearyl dimethyl sulfopropyl betaine, lauryl dimethyl sulfoethyl betaine, lauryl bis-(2-hydroxyethyl) sulfopropyl betaine and combinations thereof.

Rheology Modifier

Optionally, one or more rheology modifiers, such as thickeners, may be added to the wetting compositions. Suitable rheology modifiers are compatible with the silicone polymer. As used herein, "compatible" refers to a compound that, when mixed with the silicone polymer, does not adversely affect the properties of same.

A thickening system is used in the wetting compositions to adjust the viscosity and stability of the compositions. Specifically, thickening systems prevent the composition from running off of the hands or body during dispensing and use of the composition. When the wetting composition is used with a wipe product, a thicker formulation can be used to prevent the composition from migrating from the wipe substrate.

The thickening system should be compatible with the compounds used in the present disclosure; that is, the thickening system, when used in combination with the silicone polymer, should not precipitate out, form a coacervate, or prevent a user from perceiving the conditioning benefit (or other desired benefit) to be gained from the composition. The thickening system may include a thickener which can provide both the thickening effect desired from the thickening system and a conditioning effect to the user's skin.

Thickeners may include, cellulosics, gums, acrylates, starches and various polymers. Suitable examples include but are not limited to hydroxyethyl cellulose, xanthan gum, guar gum, potato starch, and corn starch. In some embodiments, PEG-150 stearate, PEG-150 distearate, PEG-175 diisostearate, polyglyceryl-10 behenate/eicosadioate, disteareth-100 IPDI, polyacrylamidomethylpropane sulfonic acid, butylated PVP, and combinations thereof may be suitable.

While the viscosity of the compositions will typically depend on the thickener used and the other components of the compositions, the thickeners of the compositions suitably provide for a composition having a viscosity in the range of greater than 1 cP to about 30,000 cP or more. In another embodiment, the thickeners provide compositions having a viscosity of from about 100 cP to about 20,000 cP. In yet another embodiment, thickeners provide compositions having a viscosity of from about 200 cP to about 15,000 cP. In embodiments where the compositions are included in a wipe, the viscosity may range from about 1 cP to about 2000 cP.

Typically, the wetting compositions of the present disclosure include the thickening system in an amount of no more than about 20% (by total weight of the composition), or from about 0.01% (by total weight of the composition) to about 20% (by total weight of the composition). In another aspect the thickening system is present in the wetting composition in an amount of from about 0.10% (by total weight of the composition) to about 10% (by total weight of the composition), or from about 0.25% (by total weight of the composition) to about 5% (by total weight of the composition), or from about 0.5% (by total weight of the composition) to about 2% (by total weight of the composition).

Emulsifiers

In one embodiment, the wetting compositions may include hydrophobic and hydrophilic ingredients, such as a lotion or cream. Generally, these emulsions have a dispersed phase and a continuous phase and are generally formed with the addition of a surfactant or a combination of surfactants with varying hydrophilic/lipophilic balances (HLB). Suitable emulsifiers include surfactants having HLB values from 0 to 20, or from 2 to 18. Suitable non-limiting examples include Ceteareth-20, Cetearyl Glucoside, Ceteth-10, Ceteth-2, Ceteth-20, Cocamide MEA, Glyceryl Laurate, Glyceryl Stearate, PEG-100 Stearate, Glyceryl Stearate, Glyceryl Stearate SE, Glycol Distearate, Glycol Stearate, Isosteareth-20, Laureth-23, Laureth-4, Lecithin, Methyl Glucose Sesquistearate, Oleth-10, Oleth-2, Oleth-20, PEG-100 Stearate, PEG-20 Almond Glycerides, PEG-20 Methyl Glucose Sesquistearate, PEG-25 Hydrogenated Castor Oil, PEG-30 Dipolyhydroxystearate, PEG-4 Dilaurate, PEG-40 Sorbitan Peroleate, PEG-60 Almond Glycerides, PEG-7 Olivate, PEG-7 Glyceryl Cocoate, PEG-8 Dioleate, PEG-8 Laurate, PEG-8 Oleate, PEG-80 Sorbitan Laurate, Polysorbate 20, Polysorbate 60, Polysorbate 80, Polysorbate 85, Propylene Glycol Isostearate, Sorbitan Isostearate, Sorbitan Laurate, Sorbitan Monostearate, Sorbitan Oleate, Sorbitan Sesquioleate, Sorbitan Stearate, Sorbitan Trioleate, Stearamide MEA, Steareth-100, Steareth-2, Steareth-20, Steareth-21. The compositions can further include surfactants or combinations of surfactants that create liquid crystalline networks or liposomal networks. Suitable non-limiting examples include OLIVEM 1000 (INCI: Cetearyl Olivate (and) Sorbitan Olivate (available from HallStar Company (Chicago, IL)); ARLACEL LC (INCI: Sorbitan Stearate (and) Sorbityl Laurate, commercially available from Croda (Edison, N.J.)); CRYSTALCAST MM (INCI: Beta Sitosterol (and) Sucrose Stearate (and) Sucrose Distearate (and) Cetyl Alcohol (and) Stearyl Alcohol, commercially available from MMP Inc. (South Plainfield, N.J.)); UNIOX CRISTAL (INCI: Cetearyl Alcohol (and) Polysorbate 60 (and) Cetearyl Glucoside, commercially available from Chemyunion (São Paulo, Brazil)). Other suitable emulsifiers include lecithin, hydrogenated lecithin, lysolecithin, phosphatidylcholine, phospholipids, and combinations thereof.

Adjunct Ingredients

The wetting compositions of the present disclosure may additionally include adjunct ingredients conventionally found in cosmetic, pharmaceutical, medical, or personal care compositions/products in an established fashion and at established levels. For example, the wetting compositions may comprise additional compatible pharmaceutically active and compatible materials for combination therapy, such as antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, and combinations thereof.

Other suitable additives that may be included in the wetting compositions of the present disclosure include compatible colorants, deodorants, anti-foaming agents (when foam is not desired), lubricants, skin conditioning agents, skin protectants and skin benefit agents (e.g., aloe vera and tocopheryl acetate), solvents, solubilizing agents, suspending agents, wetting agents, pH adjusting ingredients (a suitable pH range of the compositions can be from about 3.5 to about 8), chelators, propellants, dyes and/or pigments, and combinations thereof.

Another component that may be suitable for addition to the wetting compositions is a fragrance. Any compatible fragrance may be used. Typically, the fragrance is present in an amount from about 0% (by weight of the composition) to about 5% (by weight of the composition), and more typically from about 0.001% (by weight of the composition) to about 3% (by weight of the composition). In one desirable embodiment, the fragrance will have a clean, fresh and/or neutral scent to create an appealing delivery vehicle for the end consumer.

Organic sunscreens that may be present in the wetting compositions include ethylhexyl methoxycinnamate, avobenzone, octocrylene, benzophenone-4, phenylbenzimidazole sulfonic acid, homosalate, oxybenzone, benzophenone-3, ethylhexyl salicylate, and mixtures thereof.

The wetting composition may also include various preservatives to increase shelf life. Some suitable preservatives that may be used in the present disclosure include traditional preservatives. As used herein, "traditional preservatives" means compounds that have been historically recognized by regulatory bodies as providing preservative or antimicrobial effect, such as those listed in the European Union's Annex V list of preservatives allowed in cosmetics products. Traditional preservatives include, but are not limited to: propionic acid and salts thereof; salicylic acid and salts thereof; sorbic acid and salts thereof; benzoic acid and salts and esters thereof; formaldehyde; paraformaldehyde; o-phenylphenol and salts thereof; zinc pyrithione; inorganic sulfites; hydrogen sulfites; chlorobutanol; hydroxybenzoic parabens, such as methylparaben, propylparaben, butylparaben, ethylparaben, isopropylparaben, isobutylparaben, benzylparaben, sodium methylparaben and sodium propylparaben; dehydroacetic acid and salts thereof; formic acid and salts thereof; dibromohexamidine isethionate; thimerosal; phenylmercuric salts; undecylenic acid and salts thereof; hexetidine; 5-bromo-5-nitro-1,3-dioxane; 2-bromo-2-nitropropane-1,3,-diol; dichlorobenzyl alcohol; triclocarban; p-chloro-m-cresol; triclosan; chloroxylenol; imidazolidinyl urea; polyaminopropyl biguanide; phenoxyethanol, methenamine; quaternium-15; climbazole; DMDM hydantoin; benzyl alcohol; piroctone olamine; bromochlorophene; o-cymen-5-ol; methylchloroisothiazolinone; methylisothiazolinone; chlorophene; chloroacetamide; chlorhexidine; chlorhexidine diacetate; chlorhexidine digluconate; chlorhexidine dihydrochloride; phenoxyisopropanol; alkyl (C12-C22) trimethyl ammonium bromide and chlorides; dimethyl oxazolidine; diazolidinyl urea; hexamidine; hexamidine diisethionate; glutaral; 7-ethylbicyclooxazolidine; chlorphenesin; sodium hydroxymethylglycinate; silver chloride; benzethonium chloride; benzalkonium chloride; benzalkonium bromide; benzylhemiformal; iodopropynyl butylcarbamate; ethyl lauroyl arginate HCl; citric acid and silver citrate.

Other combinatorial preservatives that may be added to the wetting compositions of the present disclosure include non-traditional preservatives that are known to exhibit antimicrobial effects in addition to their primary functions, but that have not historically been recognized as preservatives by regulatory bodies (such as on the European Union's Annex V list). Examples of these non-traditional antimicrobial ingredients include, but are not limited to, hydroxyacetophenone, caprylyl glycol, sodium coco-PG dimonium chloride phosphate, phenylpropanol, lactic acid and salts thereof, caprylhydroxamic acid, levulinic acid and salts thereof, sodium lauroyl lactylate, phenethyl alcohol, sorbitan caprylate, glyceryl caprate, glyceryl caprylate, ethylhexylglycerin, p-anisic acid and salts thereof, gluconolactone, decylene glycol, 1,2-hexanediol, glucose oxidase and lactoperoxidase, leuconostoc/radish root ferment filtrate and glyceryl laurate.

The amount of the traditional and/or combinatorial preservatives in the wetting compositions is dependent on the relative amounts of other components present within the composition. For example, in some embodiments, preservatives can be present in the compositions in an amount between about 0.001% to about 5% (by total weight of the composition), in some embodiments between about 0.01 to about 3% (by total weight of the composition), and in some embodiments, between about 0.05% to about 1.0% (by total weight of the composition). In some embodiments, preservative can be present in the composition in an amount less than 0.2% (by total weight of the composition). In some embodiments, it is contemplated that the wetting composition can be substantially free of any traditional or combinatorial preservatives. As used herein, "substantially free" of any preservative means the composition includes less than 10 ppm, or 0.001% (by total weight of the composition), of a preservative.

Delivery Vehicles

The wetting compositions of the present disclosure may be used in combination with a product that can serve as a delivery vehicle for the wetting composition. For example, the wetting composition may be incorporated into or onto a substrate, such as a wipe substrate, an absorbent substrate, a fabric or cloth substrate, a tissue or paper towel substrate, or the like. In one embodiment, the wetting composition may be used in combination with a wipe substrate to form a wet wipe or may be a wetting composition for use in combination with a wipe which may be dispersible. In other embodiments, the wetting composition may be incorporated into wipes such as wet wipes, hand wipes, face wipes, cosmetic wipes, cloths and the like. In yet other embodiments, the wetting compositions described herein can be used in combination with numerous personal care products, such as absorbent articles. Absorbent articles of interest are diapers, training pants, adult incontinence products, feminine hygiene products, and the like; bath or facial tissue; and paper towels. Personal protective equipment articles of interest include but are not limited to masks, gowns, gloves, caps, and the like.

In one embodiment, the wet wipe may comprise a nonwoven material that is wetted with an aqueous solution termed the "wetting composition," which may include or be composed entirely of the wetting compositions disclosed herein. As used herein, the nonwoven material comprises a fibrous material or substrate, where the fibrous material or substrate comprises a sheet that has a structure of individual fibers or filaments randomly arranged in a mat-like fashion. Nonwoven materials may be made from a variety of processes including, but not limited to, airlaid processes, wet-laid processes such as with cellulosic-based tissues or towels, hydroentangling processes, staple fiber carding and bonding, melt blown, and solution spinning.

When the wetting composition is added to a delivery vehicle, such as a wipe substrate, the amount of add-on of the wetting composition can range from about 100% to about 400%, or more preferably from about 200% to about 375%, or even more preferably from about 240% to about 350%. In some embodiments, the add-on of the wetting composition can be from 200% to about 350%. In one particular embodiment, the add-on can be about 330%.

The fibers forming the fibrous material may be made from a variety of materials including natural fibers, synthetic fibers, and combinations thereof. The choice of fibers may depend upon, for example, the intended end use of the finished substrate and the fiber cost. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or crosslinked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber.

Airlaid nonwoven fabrics are particularly well suited for use as wet wipes. The basis weights for airlaid nonwoven fabrics may range from about 20 to about 200 grams per square meter (gsm) with staple fibers having a denier of about 0.5 to about 10 and a length of about 6 to about 15 millimeters. Wet wipes may generally have a fiber density of about 0.025 g/cc to about 0.2 g/cc. Wet wipes may generally have a basis weight of about 20 gsm to about 150 gsm. More desirably the basis weight may be from about 30 to about 90 gsm. Even more desirably the basis weight may be from about 50 gsm to about 75 gsm.

Processes for producing airlaid non-woven basesheets are described in, for example, published U.S. Pat. App. No. 2006/0008621, herein incorporated by reference to the extent it is consistent herewith.

EXAMPLES

A variety of exemplary silicone polymer softening agents were synthesized for testing in a wetting composition, as shown in Table 1. The exemplary silicone polymer softening agents from Examples 1-7 shown below were used in an exemplary wetting composition formulated as shown in Table 1, and also an exemplary dispersible wetting composition as shown in Table 2.

TABLE 1

Components of exemplary wetting composition.

| Trade Name | Manufacturer | INCI Name | % wt/wt |
|---|---|---|---|
| PART A | | | |
| Water | N/A | Water | 99.018 |
| Malic Acid FCC | Jungbunzlauer | Malic Acid | 0.055 |
| PART B | | | |
| Exemplary Silicone Polymer Code (from Table 2) | Siltech Corporation | Butoxy PEG-4 PG-Amodimethicone | 0.300 |
| PART C | | | |
| Lexgard O | Inolex | Caprylyl Glycol | 0.100 |
| Dehyton AB-30 | BASF | Coco-Betaine | 0.300 |
| Kalama Sodium Benzoate NF/FCC | Emerald Performance Materials | Sodium Benzoate | 0.100 |
| Eumulgin SML-20 | BASF | Polysorbate 20 | 0.060 |
| DL-Alpha-Tocopheryl Acetate | DSM | Tocopheryl Acetate | 0.001 |
| Aloe Vera 1:200 Powder | Aloe Corp | Aloe Barbadensis Leaf Juice | 0.001 |
| Trisodium Citrate Dihydrate F6000 | Jungbunzlauer | Sodium Citrate | 0.010 |
| PART D | | | |
| Malic Acid FCC | Jungbunzlauer | Malic Acid | 0.055 |

The procedure for making the wetting composition from Table 1 for testing herein includes the following steps:
  Charge beaker with water
  Add PART A and mix until dissolved
  Add PART B and mix until dissolved or uniform in appearance
  Add ingredients of PART C in order with complete dissolution of each
  Add PART D; adjust amount to achieve target pH of 4.20±0.10

The silicone polymers were also tested for various properties when used in a dispersible wetting composition. An exemplary dispersible wetting composition is shown in Table 2.

TABLE 2

Components of exemplary dispersible wetting composition.

| Trade Name | Manufacturer | INCI Name | % wt/wt |
|---|---|---|---|
| PART A | | | |
| Water | N/A | Water | 97.018 |
| Malic Acid FCC | Jungbunzlauer | Malic Acid | 0.055 |
| PART B | | | |
| Exemplary Silicone Polymer Code (from Table 2) | Siltech Corporation | Butoxy PEG-4 PG-Amodimethicone | 0.300 |
| PART C | | | |
| Lexgard O | Inolex | Caprylyl Glycol | 0.100 |
| Dehyton AB-30 | BASF | Coco-Betaine | 0.300 |
| Kalama Sodium Benzoate NF/FCC | Emerald Performance Materials | Sodium Benzoate | 0.100 |

TABLE 2-continued

Components of exemplary dispersible wetting composition.

| Trade Name | Manufacturer | INCI Name | % wt/wt |
|---|---|---|---|
| Eumulgin SML-20 | BASF | Polysorbate 20 | 0.060 |
| DL-Alpha-Tocopheryl Acetate | DSM | Tocopheryl Acetate | 0.001 |
| Aloe Vera 1:200 Powder | Aloe Corp | Aloe Barbadensis Leaf Juice | 0.001 |
| Trisodium Citrate Dihydrate F6000 | Jungbunzlauer | Sodium Citrate | 0.010 |
| PART D | | | |
| Sodium Chloride | Cargill Foods | Sodium Chloride | 2.00 |
| PART E | | | |
| Malic Acid FCC | Jungbunzlauer | Malic Acid | 0.055 |

The procedure for making the dispersible wetting composition from Table 2 includes the following steps:

Charge beaker with water
Add PART A and mix until dissolved
Add PART B and mix until dissolved or uniform in appearance
Add ingredients of PART C in order with complete dissolution of each
Add PART D and mix until dissolved
Add PART E; adjust amount to achieve target pH of 4.20±0.10

Seven different silicone polymer softening agent codes were tested for solubility in exemplary wetting compositions (as made according to Table 1) according to the Solubility Test Method and for softness benefit perception according to the Softness Benefit Perception Test Method described in the Test Methods section herein. For the softness benefit perception testing, the exemplary wetting compositions were put into a wipe substrate composed of 55 gsm coform with 270% add-on. Table 2 below shows the seven codes that were tested, as well as the results.

TABLE 3

Testing of various exemplary silicone polymer softening agents in wetting composition.

| Code No. | Tradename | x | y | z | Ratio x:(y + z) | a | b | n | Molecular Weight (g/mol) | Solubility in wetting composition (0.3% w/w) | Softness Benefit Perception |
|---|---|---|---|---|---|---|---|---|---|---|---|
| 1 | Silamine ® F904A | 54 | 5 | 1 | 9:1 | 2 | 4 | 2 | 5853 | insoluble | n/a |
| 2 | Silamine ® F908A | 54 | 5 | 1 | 9:1 | 2 | 8 | 2 | 6733 | insoluble | n/a |
| 3 | Silamine ® E408A | 20 | 4 | 1 | 4:1 | 2 | 8 | 2 | 3800 | soluble, transparent | yes, but weak |
| 4 | Silamine ® J1008A | 100 | 9 | 1 | 10:1 | 2 | 8 | 2 | 10717 | insoluble | n/a |
| 5 | Silamine ® E404A | 20 | 4 | 1 | 4:1 | 2 | 4 | 2 | 3056 | soluble, very hazy but homogeneous | yes |
| 6 | Silamine ® F304A | 18 | 5 | 1 | 3:1 | 2 | 4 | 2 | 3189 | soluble, slightly hazy but homogeneous | yes |
| 7 | Silamine ® E204A | 10 | 4 | 1 | 2:1 | 2 | 4 | 2 | 2300 | soluble, transparent | yes, but weak |

As documented in Table 3, several silicone polymer agents were soluble within water. In particular, code nos. 5 and 6 were the most preferable as they were water soluble and provided at least a slightly hazy, or very hazy, homogeneous wetting composition after the Solubility Test. Additionally, several of the exemplary codes provided at least some softness benefit perception according to the Softness Benefit Test. Code nos. 5 and 6 were the strongest codes for providing

TEST METHODS

Solubility Test

The solubility test is conducted by visual inspection of the exemplary wetting composition at ambient temperature immediately after the wetting composition was formulated with the silicone polymers according to the exemplary procedures as described herein, and then at a second instance two hours after the initial formulation. The solubility was assessed based on a first determination of soluble, or insoluble. If an exemplary wetting composition was determined to be soluble, further visual inspection was conducted as to the nature of the composition, such as whether the composition was transparent, hazy, and/or homogeneous. No results in solubility were documented as changing from the immediate inspection to the inspection at two hours from formulation.

Softness Benefit Perception Test

The softness benefit perception test is conducted by folding a wet wipe sample of a substrate including an exemplary wetting composition in half and keeping the wipe at the tester's fingers. The arm of the tester not holding the folded wipe is at the tester's side with a 90° bend in such arm, with the forearm of the free arm rotated such that the hand on the free arm is facing up. Starting with the fingers of the hand holding the folded wipe positioned at wrist of the free arm and the open end of the fold of the wipe facing the hand of the free arm, the tester runs the wipe from wrist to elbow on the free arm with light pressure three times. From this wiping motion, the tester provides a softness perception analysis of the wipe between the forearm of the free arm and the folded wipe.

EMBODIMENTS

Embodiment 1

A wetting composition comprising: water in an amount of at least 75% of the wetting composition; and a softening agent having the following structure:

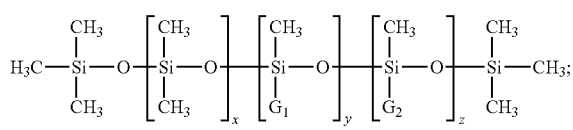

wherein $G_1$ comprises —$CH_2CH_2CH_2$—$(C_aH_{2a}O)_b$—H; and wherein $G_2$ comprises —$CH_2CH_2CH_2$—$OCH_2$—CH(OH)—$CH_2$—$R_1$, wherein $R_1$ is selected from the group consisting of: —NH—$(CH_2)_n$—$NH_2$, —NH—$(CH_2)_n$—NH—$(CH_2)_m$—$NH_2$, N-piperidine, and N-3,3,5,5-tetramethyl-piperidine.

Embodiment 2

The wetting composition of embodiment 1, wherein x is at least 2 and is less than or equal to 50.

Embodiment 3

The wetting composition of any one of the preceding embodiments, wherein y is at least 1 and is less than 7.

Embodiment 4

The wetting composition of any one of the preceding embodiments, wherein z is at least 1 and is less than 5.

Embodiment 5

The wetting composition of any one of the preceding embodiments, wherein a ratio of x to (y+z) is at least 2:1 and is less than 9:1.

Embodiment 6

The wetting composition of any one of the preceding embodiments, wherein at least one $G_1$ unit is configured such that a equals 2.

Embodiment 7

The wetting composition of any one of the preceding embodiments, wherein at least one $G_1$ unit is configured such that a equals 3.

Embodiment 8

The wetting composition of any one of the preceding embodiments, wherein y is at least two, and wherein at least one $G_1$ unit is configured such that a equals 2 and at least one $G_1$ unit is configured such that a equals 3.

Embodiment 9

The wetting composition of any one of the preceding embodiments, wherein at least one $G_1$ unit is configured such that b is at least 1 and is less than 25.

Embodiment 10

The wetting composition of any one of the preceding embodiments, wherein at least one $G_2$ unit is configured such that n in $R_1$ is at least 2 and is less than 7.

Embodiment 11

The wetting composition of any one of the preceding embodiments, wherein at least one $G_2$ unit is configured such that m in $R_1$ is at least 2 and is less than 7.

Embodiment 12

The wetting composition of any one of the preceding embodiments, wherein at least one $G_2$ unit is —NH—$(CH_2)_2$—$NH_2$.

Embodiment 13

A wetting composition comprising: water in an amount of at least 75% of the wetting composition; and a softening agent having the following structure:

19

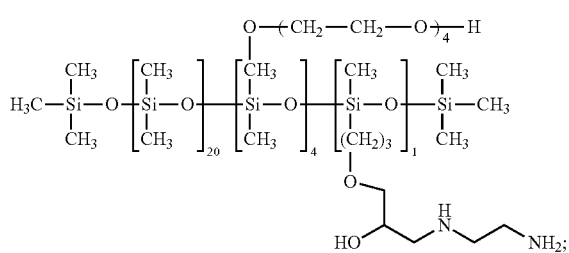

wherein x is at least 2 and is less than or equal to 50; wherein y is at least 1 and is less than 7; and wherein z is at least 1 and is less than 5.

Embodiment 14

A wet wipe comprising: a substrate; and a wetting composition comprising: water; and a softening agent having the following structure:

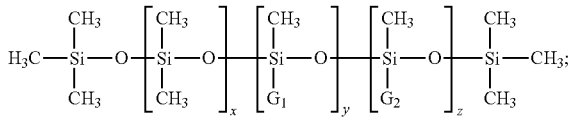

wherein $G_1$ comprises —$CH_2CH_2CH_2$—$(C_aH_{2a}O)_b$—H; and wherein $G_2$ comprises —$CH_2CH_2CH_2$—$OCH_2$—CH(OH)—$CH_2$—$R_1$, wherein $R_1$ is selected from the group consisting of: —NH—$(CH_2)_n$—$NH_2$, —NH—$(CH_2)_n$—NH—$(CH_2)_m$—$NH_2$, N-piperidine, and N-3,3,5,5-tetramethyl-piperidine.

Embodiment 15

The wet wipe of embodiment 14, wherein x is at least 2 and is less than or equal to 50.

Embodiment 16

The wet wipe of embodiment 14 or 15, wherein y is at least 1 and is less than 7.

Embodiment 17

The wet wipe of any one of embodiments 14-16, wherein z is at least 1 and is less than 5.

Embodiment 18

The wet wipe of any one of embodiments 14-17, wherein at least one $G_1$ unit is configured such that a equals 2.

Embodiment 19

The wet wipe of any one of embodiments 14-18, wherein at least one $G_1$ unit is configured such that b is at least 1 and is less than 25.

Embodiment 20

The wet wipe of any one of embodiments 14-19, wherein at least one $G_2$ unit is configured such that n in $R_1$ is at least 2 and is less than 7, and wherein at least one $G_2$ unit is configured such that m in $R_1$ is at least 2 and is less than 7.

20

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the disclosure.

What is claimed is:

1. A wetting composition comprising:
   water in an amount of at least 75% of the wetting composition; and
   a softening agent having the following structure:

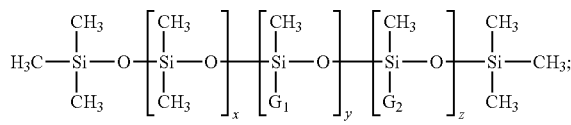

wherein $G_1$ comprises —$CH_2CH_2CH_2$—$(C_aH_{2a}O)_b$—H; and wherein $G_2$ comprises —$CH_2CH_2CH_2$—$OCH_2$—CH(OH)—$CH_2$—$R_1$, wherein $R_1$ is selected from the group consisting of: —NH—$(CH_2)_n$—$NH_2$, —NH—$(CH_2)_n$—NH—$(CH_2)_m$—$NH_2$, N-piperidine, and N-3,3,5,5-tetramethyl-piperidine, wherein a first functional unit comprises x units in the structure, a second functional unit comprises the G1 unit and comprises y units in the structure and a third functional unit comprises the G2 unit and comprises z units in the structure.

2. The wetting composition of claim 1, wherein x is at least 2 and is less than or equal to 50.

3. The wetting composition of claim 1, wherein y is at least 1 and is less than 7.

4. The wetting composition of claim 1, wherein z is at least 1 and is less than 5.

5. The wetting composition of claim 1, wherein a ratio of x to (y+z) is at least 2:1 and is less than 9:1.

6. The wetting composition of claim 1, wherein at least one $G_1$ unit is configured such that a equals 2.

7. The wetting composition of claim 1, wherein at least one $G_1$ unit is configured such that a equals 3.

8. The wetting composition of claim 1, wherein y is at least two, and wherein at least one $G_1$ unit is configured such that a equals 2 and at least one $G_1$ unit is configured such that a equals 3.

9. The wetting composition of claim 1, wherein at least one $G_1$ unit is configured such that b is at least 1 and is less than 25.

10. The wetting composition of claim 1, wherein at least one $G_2$ unit is configured such that n in $R_1$ is at least 2 and is less than 7.

11. The wetting composition of claim 1, wherein at least one $G_2$ unit is configured such that m in $R_1$ is at least 2 and is less than 7.

12. The wetting composition of claim 1, wherein at least one $G_2$ unit is —NH—$(CH_2)_2$—$NH_2$.

13. A wetting composition comprising:
    water in an amount of at least 75% of the wetting composition; and
    a softening agent having the following structure:

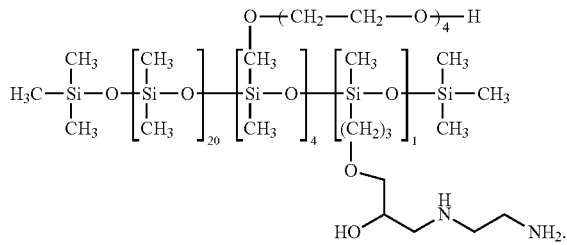

14. A wet wipe comprising:
    a substrate; and
    a wetting composition comprising:
        water; and
        a softening agent having the following structure:

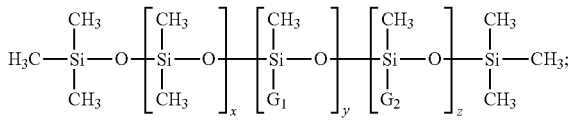

wherein $G_1$ comprises —$CH_2CH_2CH_2$—$(C_aH_{2a}O)_b$—H; and wherein $G_2$ comprises —$CH_2CH_2CH_2$—$OCH_2$—CH(OH)—$CH_2$—$R_1$, wherein $R_1$ is selected from the group consisting of: —NH—$(CH_2)_n$—$NH_2$, —NH—$(CH_2)_n$—NH—$(CH_2)_m$—$NH_2$, N-piperidine, and N-3,3,5,5-tetramethyl-piperidine, wherein a first functional unit comprises x units in the structure, a second functional unit comprises the G1 unit and comprises y units in the structure and a third functional unit comprises the G2 unit and comprises z units in the structure.

15. The wet wipe of claim 14, wherein x is at least 2 and is less than or equal to 50.

16. The wet wipe of claim 14, wherein y is at least 1 and is less than 7.

17. The wet wipe of claim 14, wherein z is at least 1 and is less than 5.

18. The wet wipe of claim 14, wherein at least one $G_1$ unit is configured such that a equals 2.

19. The wet wipe of claim 14, wherein at least one $G_1$ unit is configured such that b is at least 1 and is less than 25.

20. The wet wipe of claim 14, wherein at least one $G_2$ unit is configured such that n in $R_1$ is at least 2 and is less than 7, and wherein at least one $G_2$ unit is configured such that m in $R_1$ is at least 2 and is less than 7.

* * * * *